United States Patent [19]

Egraz et al.

[11] Patent Number: 5,294,693
[45] Date of Patent: Mar. 15, 1994

[54] ACRYLIC COPOLYMER WHICH IS WATER-SOLUBLE OR MODERATELY WATER-SOLUBLE AND MAY BE CROSSLINKED; AND ITS USE

[75] Inventors: Jean-Bernard Egraz, Ecully; Henri Grondin; Jean-Marc Suau, both of Lyons, all of France

[73] Assignee: Coatex S.A., Genay, France

[21] Appl. No.: 83,257

[22] Filed: Jun. 29, 1993

[30] Foreign Application Priority Data

Jul. 1, 1992 [FR] France ................... 92 08399

[51] Int. Cl.$^5$ ............................................ C08F 20/26
[52] U.S. Cl. ................................ 526/310; 526/312;
526/317.1; 526/318.2; 526/318.3; 526/318.4;
526/320; 526/329.2; 526/329.3; 526/330
[58] Field of Search ............... 526/317.1, 318.2, 318.3,
526/310, 312, 329.3, 330, 329.2, 320, 318.4

[56] References Cited

U.S. PATENT DOCUMENTS 4,921,902 5/1990 Evani et al. ................. 526/320

FOREIGN PATENT DOCUMENTS 0003235 8/1979 European Pat. Off. .
0011806 6/1980 European Pat. Off. .
0013836 8/1980 European Pat. Off. .

*Primary Examiner*—Joseph L. Schofer
*Assistant Examiner*—Jeffrey T. Smith
*Attorney, Agent, or Firm*—Oblon, Spivak, McClelland, Maier & Neustadt

[57] ABSTRACT

A copolymer comprised of at least one monomer having ethylenic unsaturation and a carboxylic acid group, optionally at least one monomer having ethylenic unsaturation and not having a carboxylic acid group, at least one oxyalkylated monomer having ethylenic unsaturation and terminated by a fatty hydrophobic chain having at least 26 C atoms, and optionally at least one monomer having at least two sites of ethylenic unsaturation. The copolymer is employed as a modifier of rheological properties, stabilizing agent, and/or an antisedimentation or suspension agent for coarse mineral or organic materials, in applications such as drilling muds, textile printing pies, cosmetics, detergents, plant protection, and paints and coatings.

12 Claims, No Drawings

ACRYLIC COPOLYMER WHICH IS WATER-SOLUBLE OR MODERATELY WATER-SOLUBLE AND MAY BE CROSSLINKED; AND ITS USE

BACKGROUND OF THE INVENTION

1. Field of the Invention

The present invention relates to a copolymer which is water-soluble or moderately water-soluble and which may be crosslinked.

The invention also relates to the use of the described copolymer as a rheological modifier in very diverse applications, such as drilling muds, textile printing pies, cosmetics, detergents, various other coating compositions such as paints, and as an antisedimentation and/or suspension agent for mineral or organic materials, in various areas of technology, such as, e.g., plant protection.

2. Description of the Background

Copolymers formed from monomers, one of which has a carboxyl group (or groups), and the second of which does not, are known as copolymers which confer distinct rheological properties on aqueous formulations which increase the viscosity thereof. Thus, Eur. Pat. 0,173,109 describes a copolymer comprised of units of an ethylenically unsaturated carboxylic acid, units of an ethylenically unsaturated ester, and units of a third monomer which is the product of the reaction of a fatty alcohol having 6-22 C atoms with an unsaturated isocyanate.

Eur. Pat. 0,013,836 discloses, although only very generally, a copolymer based on methacrylic acid, an alkyl acrylate having up to 4 C atoms, and an oxyalkylated monomer terminated by a fatty chain having up to 30 C atoms. Eur. Pat. 0,011,806 describes the same type of copolymer wherein the third monomer is an ethylenically unsaturated monomer and is terminated by a fatty chain having up to 20 C atoms. Eur. Pat. 0,248,612 claims a copolymer wherein the third monomer is an ester having a fatty chain containing up to 25 C atoms.

Further, Eur. Pat. 0,216,479 describes, although only very generally, a copolymer based on an ionic ethylenically unsaturated monomer, a substantially nonionic ethylenically unsaturated monomer, an oxyalkylated allyl ether having up to 30 C atoms, and a crosslinking agent.

All of the publications describe polymers which do not perform entirely satisfactorily when employed in certain formulations, however. A need therefore continues to exist for a method of increasing the "apparent viscosity" of aqueous suspensions at low shear gradient to confer excellent stability on aqueous suspensions of mineral or organic materials, particularly antisedimentation stability, without a correspondingly large increase in the viscosity such as is frequently experienced with polymers known to the art.

SUMMARY OF THE INVENTION

Accordingly, one object of the present invention is to provide a copolymer which functions to increase the apparent viscosity of aqueous suspensions at low shear gradients and which confers excellent stability to aqueous suspensions of organic and mineral materials.

Briefly, this object and other objects of the present invention as hereinafter will become more readily apparent can be attained by a copolymer of the formula:

$$A_a\text{-}B_b\text{-}C_c\text{-}D_d,$$

where
- A represents units of ethylenically unsaturated monomer or monomers having a carboxylic acid group where a represents the percent by weight (wt.%) of the monomer A on the basis of the total weight of the monomer units;
- B represents units of ethylenically unsaturated monomer or monomers not having a carboxylic acid group, where b represents the percent by weight (wt.%) of the monomer B on the basis of the total weight of the monomers, wherewith optionally b may be zero;
- C represents an ethylenically unsaturated oxyalkylated monomer terminated by a hydrophobic fatty chain having at least 26 C atoms, where c represents the percent by weight (wt.%) of the monomer on the basis of the total weight of the monomers, wherewith the monomer will be referred to hereinbelow as the "special monomer", and is described by the formula I:

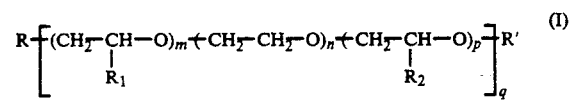

here
- m and p represent numbers of oxyalkylene groups;
- n represents the number of oxyethylene groups;
- q represents a number at least equal to 1, such that $q(n+m+p) \leq 100$;
- R represents an unsaturated polymerizable group;
- R' represents a hydrophobic group with a fatty chain having at least 26 C atoms;
- $R_1$ represents hydrogen or a methyl group; and
- $R_2$ represents hydrogen or a methyl group; and
- D represents units of a monomer or monomers containing at least two sets of ethylenic unsaturations, where d represents the percent by weight (wt.%) of the monomer D on the basis of the total weight of the monomers, wherewith optionally d may be zero; and with the constraint that $a+b+c+d=100\%$.

DETAILED DESCRIPTION OF THE PREFERRED EMBODIMENTS

The copolymer of the present invention is distinguished by the fact that it is comprised of:

(a) units of at least one ethylenically unsaturated monomer and having one or more carboxylic acid groups, which monomer is selected from among the monoacids such as acrylic, methacrylic, crotonic, isocrotonic, and cinnamic acid; the diacids such as itaconic, fumaric, maleic, and citraconic acids; the anhydrides of carboxylic acids such as maleic anhydride, and the hemiesters of diacids, such as the $C_1$-$C_4$ monoesters of maleic and itaconic acid, with the preferred ethylenically unsaturated carboxyl-group-containing (carboxylated) monomer being acrylic acid, methacrylic acid, or itaconic acid;

(b) optionally, unit(s) of at least one ethylenically unsaturated monomer not having a carboxylic acid group, selected in a non-limiting manner from the group consisting of esters of (meth)acrylic acid such as methyl, ethyl, butyl, or 2-ethylhexyl (meth)acrylate, or from the group consisting of acrylonitrile, vinyl acetate, styrene, methylstyrene, diisobutylene, vinylpyrrolidone, and vinylcaprolactam; preferably with the ethylenically unsaturated non-carboxylated monomer being selected from the group consisting of acrylic esters such as the $C_1$–$C_4$-alkyl (meth)acrylates;

(c) units of at least one monomer designated a "special monomer", which is an oxyalkylated monomer having ethylenic unsaturation and which is terminated by a hydrophobic fatty chain, said monomer having formula I:

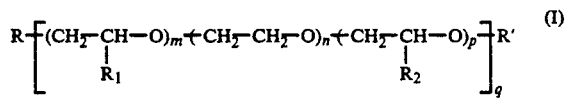

where m and p represent numbers of oxyalkylene groups, each $\leq 100$;

n represents the number of oxyethylene groups $\leq 100$;

q represents a number at least equal to 1, such that $q(n+m+p) \leq 100$;

$R_1$ represents hydrogen or a methyl group;

$R_2$ represents hydrogen or a methyl group; and

R represents an unsaturated polymerizable group selected from the group consisting of vinyl group containing moieties, methacryloyl, maleoyl, itaconoyl, crotonyl, an unsaturated urethane moiety, hemiester maleoyl, hemiester itaconoyl, $CH_2=CHCH_2-O-$, methacrylamido and substituted methacrylamido; and R' represents a hydrophobic group with a fatty chain, such as an alkyl, alkylaryl, aralkyl, or aryl group, linear or branched, and having at least 26 C atoms, preferably at least 30 C atoms;

or, preferably, R' represents a hydrophobic alkyl group (linear or branched) with 28 C atoms, wherewith the number of oxyalkylene groups is in the range 10–70; and (d) optionally, unit(s) of at least one monomer having at least two sites of ethylenic unsaturation such as ethylene glycol dimethacrylate, 2,2-dihydroxymethylbutanol triacrylate, allyl acrylate, methylenebis(meth)acrylamide, tetraallyloxyethane, the triallyl cyanurates, and the various allyl ethers obtained from polyols such as pentaerythritol, sorbitol, sucrose, or others.

The vinyl group containing moiety of R is preferably a member selected from the group consisting of acryloyl, a vinylphthaloyl, a hemiester phthaloyl, acrylamido and a substituted acrylamido, and the unsaturated urethane moiety is preferably (meth)acrylurethane, α,α-dimethyl-m-isopropenylbenzylurethane or allylurethane.

The copolymer according to the invention, obtained by known methods of radical copolymerization in solution, direct or inverse emulsion, in suspension, or via precipitation in suitable solvents, in the presence of known catalysts and transfer agents, preferably has a composition as follows:

a. 15–98 wt.%, particularly preferably 20–50 wt.%, of units of ethylenically unsaturated monomers having at least one carboxylic acid group;

b. 0–83 wt.%, particularly preferably 47–77 wt.%, of unit(s) of other monomer(s) having ethylenic unsaturation and not having any carboxylic acid groups;

c. 2–18 wt.%, particularly preferably 3–10 wt.%, of units of a "special monomer"; and d. 0–5 wt.%, particularly preferably 0–3 wt.%, of unit(s) of monomer(s) having at least two sites of ethylenic unsaturation; wherewith the total of components (a.)+(b.)+(c.)+(d.)=100 wt.%.

The invention also relates to aqueous formulations containing fillers and/or pigments and a copolymer embodiment of the invention. The aqueous formulations containing fillers and/or pigments are particularly those containing, in addition to the copolymer of the invention, a mineral filler such as calcium carbonate, clays, iron oxides, sodium silica-aluminates or zeolites, and/or one or more colorants, and optionally a natural or synthetic binder and other constituents such as dispersants, coalescing agents, biocides, surfactants, and antifoamants.

Among all of the types of aqueous formulations containing a copolymer of the invention, one might mention, e.g., cosmetic formulations, textile printing pies, aqueous suspensions of zeolites, drilling muds (particularly aqueous drilling muds), paste-type cleansers, detergents, and paints and other coatings.

Having now generally described this invention, a further understanding can be obtained by reference to certain specific examples which are provided herein for purposes of illustration only and are not intended to be limiting unless otherwise specified.

EXAMPLE 1

To compare the thickening power of various thickeners under conditions of low shear gradient, 0.5 wt.% solutions of various polymers (on a dry polymer basis) were prepared and were neutralized to pH 8.5 with the aid of 28% ammonia. The solutions were then allowed to stand 24 hr.

At the end of 24 hrs, the apparent viscosities of these gels were determined at 25° C. with the aid of a "Rheomat 115" viscosimeter (supplied by the firm Contraves), equipped with a "145" mobile and set up for shear rates of 0.1 and 0.5 sec$^{-1}$. In all of the tests of Example 1, the copolymers studied had the following basic composition:

a. 36 wt.% units of methacrylic acid;
b. 55 wt.% units of ethyl acrylate; and
c. 9 wt.% units of a "special monomer" of formula I.

In particular the test substances were as follows:

Test No. 1

A copolymer known to the art, wherein the "special monomer" of formula I is a hemimaleate comprised of 25 oxyethylene groups and a linear alkyl group R' comprised of 12 C atoms.

Test No. 2

A copolymer known to the art, wherein the "special monomer" of formula I is a hemimaleate comprised of 25 oxyethylene groups and a linear alkyl group R' comprised of 16–18 C atoms.

Test No. 3

A copolymer known to the art, wherein the "special monomer" of formula I is a hemimaleate comprised of 25 oxyethylene groups and an alkyl group R' comprised of 22 C atoms.

Test No. 4

A copolymer of the invention, wherein the "special monomer" of formula I is a hemimaleate comprised of 25 oxyethylene groups and an alkyl group R, comprised of 28 C atoms.

Test No. 5

A copolymer of the invention, wherein the "special monomer" of formula I is a hemimaleate comprised of 25 oxyethylene groups and an alkyl group R, comprised of 32 C atoms.

Test No. 6

A copolymer of the invention, wherein the "special monomer" of formula I is a hemimaleate comprised of 25 oxyethylene groups and an alkyl group R, comprised of 34 C atoms.

Test No. 7

A copolymer of the invention, wherein the "special monomer" of formula I is a hemimaleate comprised of 25 oxyethylene groups and an alkyl group R, comprised of 36 C atoms.

Test No. 8

A copolymer known to the art, wherein the "special monomer" of formula I is a methacrylate comprised of 25 oxyethylene groups and a linear alkyl group R, comprised of 12 C atoms.

Test No. 9

A copolymer known to the art, wherein the "special monomer" of formula I is a methacrylate comprised of 25 oxyethylene groups and a linear alkyl group R, comprised of 16–18 C atoms.

Test No. 10

A copolymer known to the art, wherein the "special monomer" of formula I is a methacrylate comprised of 25 oxyethylene groups and an alkyl group R, comprised of 22 C atoms.

Test No. 11

A copolymer of the invention, wherein the "special monomer" of formula I is a methacrylate comprised of 25 oxyethylene groups and an alkyl group R, comprised of 32 C atoms.

Test No. 12

A copolymer of the invention, wherein the "special monomer" of formula I is a methacrylate comprised of 25 oxyethylene groups and an alkyl group R, comprised of 34 C atoms.

Test No. 13

A copolymer of the invention, wherein the "special monomer" of formula I is a methacrylate comprised of 25 oxyethylene groups and an alkyl group R, comprised of 36 C atoms.

The results of the measurements of the apparent viscosities (Pa-s) at the various shear rates ($^{-1}$) are summarized, for all of the tests, in Table I infra.

TABLE I

| | Test No. | MONOMER OF FORMULA I | | | | | | | | SHEAR RATE ($s^{-1}$) | |
|---|---|---|---|---|---|---|---|---|---|---|---|
| | | m | n | p | q | $R_1$ | $R_2$ | R | R' | 0.1 $\eta$ Pa·s | 0.5 $\eta$ Pa·s |
| A.A. | 1 | 0 | 25 | 0 | 1 | — | — | hemimaleate | $C_{12}$ alkyl | 5.75 | 1.15 |
| A.A. | 2 | 0 | 25 | 0 | 1 | — | — | hemimaleate | cetyl-stearyl | 6.23 | 1.25 |
| A.A. | 3 | 0 | 25 | 0 | 1 | — | — | hemimaleate | $C_{22}$ alkyl | 5.27 | 1.92 |
| INV. | 4 | 0 | 25 | 0 | 1 | — | — | hemimaleate | $C_{28}$ alkyl | 52 | 26 |
| INV. | 5 | 0 | 25 | 0 | 1 | — | — | hemimaleate | $C_{32}$ alkyl | 54 | 13 |
| INV. | 6 | 0 | 25 | 0 | 1 | — | — | hemimaleate | $C_{34}$ alkyl | 49 | 13 |
| INV. | 7 | 0 | 25 | 0 | 1 | — | — | hemimaleate | $C_{36}$ alkyl | 24 | 7 |
| A.A. | 8 | 0 | 25 | 0 | 1 | — | — | methacrylate | $C_{12}$ alkyl | 0.48 | 0.19 |
| A.A. | 9 | 0 | 25 | 0 | 1 | — | — | methacrylate | cetyl-stearyl | 42.2 | 14.5 |
| A.A. | 10 | 0 | 25 | 0 | 1 | — | — | methacrylate | $C_{22}$ alkyl | 40 | 12.3 |
| INV. | 11 | 0 | 25 | 0 | 1 | — | — | methacrylate | $C_{32}$ alkyl | 115 | 37.5 |
| INV. | 12 | 0 | 25 | 0 | 1 | — | — | methacrylate | $C_{34}$ alkyl | 73.3 | 19.4 |
| INV. | 13 | 0 | 25 | 0 | 1 | — | — | methacrylate | $C_{36}$ alkyl | 56 | 15 |

$\eta$ = apparent viscosity
A.A. = Known Copolymer
INV. = Invention

It is clear from Table I that for Tests Nos. 4–7 and 11–13 the thickening of the gel achieved with 0.5 wt.% of polymer (dry polymer basis) is clearly superior when the copolymers of the invention are used, which are comprised of
- methacrylic acid,
- ethyl acrylate, and
- an oxyalkylated monomer having ethylenic unsaturation and terminated with a hydrophobic fatty chain, the monomer being represented by formula I, wherein R, represents a hydrophobic group having at least 26 C atoms.

EXAMPLE 2

This example concerns thickening of a shampoo base containing ammonium lauryl ether sulfate and silicones.

Procedure

The base to be thickened is introduced into a glass bottle and agitated very slowly with the aid of an agitation system of the Rayneri type. The following were introduced successively:
i) 250 g of the shampoo base to be thickened;
ii) 25 g water of industrial quality;
iii) 5 g of the thickener to be tested (containing 30 wt.% of active material).

The pH was adjusted to 6.5 with the aid of triethanolamine.

For producing the formulation it is necessary to prepare a mixture which is suitably thick and also perfectly clear and transparent. The apparent viscosity is measured with a Brookfield viscosimeter of type "RVT" equipped with a module adapted to 20° C.

The readings were taken at 10 and 100 rpm, immediately after preparation of the mixture and again after an interval of 40 hr.

The particular test substances, in the form of copolymers employed as thickeners, were as follows:

Test No. 14

A copolymer known to the art, comprised of:
a. 36 wt.% of units of methacrylic acid;
b. 55 wt.% of units of ethyl acrylate;
c. 9 wt.% of units of a methacrylate comprised of 50 oxyethylene groups and a linear alkyl group R, having 16–18 C atoms.

Test No. 15

A copolymer known to the art, comprised of:
a. 36 wt.% of units of methacrylic acid;
b. 55 wt.% of units of ethyl acrylate;
c. 9 wt.% of units of a methacrylate comprised of 20 oxyethylene groups and an alkyl group R, having 22 C atoms.

Test No. 16

A copolymer known to the art, comprised of:
a. 36 wt.% of units of methacrylic acid;
b. 55 wt.% of units of ethyl acrylate;
c. 9 wt.% of units of a methacrylate comprised of 50 oxyethylene groups and an alkylaryl group R, such as nonylphenyl.

Test No. 17

A copolymer known to the art, comprised of:
a. 36 wt.% of units of methacrylic acid;
b. 55 wt.% of units of ethyl acrylate;
c. 9 wt.% of units of a methacrylate comprised of 35 oxyethylene groups and an alkyl group R' having 22 C atoms.

Test No. 18

A copolymer of the present invention, comprised of:
a. 36 wt.% of units of methacrylic acid;
b. 55 wt.% of units of ethyl acrylate;
c. 9 wt.% of units of a methacrylate comprised of 25 oxyethylene groups and an alkyl group R' having 32 C atoms.

Test No. 19

A copolymer of the present invention, comprised of:
a. 36 wt.% of units of methacrylic acid;
b. 55 wt.% of units of ethyl acrylate;
c. 9 wt.% of units of a methacrylate comprised of 25 oxyethylene groups and an alkyl group R' having 34 C atoms.

Test No. 20

A copolymer of the present invention, comprised of:
a. 36 wt.% of units of methacrylic acid;
b. 55 wt.% of units of ethyl acrylate;
c. 9 wt.% of units of a methacrylate comprised of 15 oxyethylene groups and an alkyl group R' having 34 C atoms.

The results of the measurements of the Brookfield viscosities of the various test samples are summarized in Table II, infra.

TABLE II

| | TEST NO. | \multicolumn{7}{c|}{MONOMER OF FORMULA I} | $\eta$ IMMEDIATE mPa·s | | $\eta$ 48 HOURS mPa·s | | APPEARANCE OF GEL |
|---|---|---|---|---|---|---|---|---|---|---|---|---|---|
| | | m | n | p | q | $R_1$ | $R_2$ | R' | 10 rpm | 100 rpm | 10 rpm | 100 rpm | |
| A.A. | 14 | 0 | 50 | 0 | 1 | — | — | cetyl-stearyl | 600 | 560 | 1300 | 1050 | cloudy |
| A.A. | 15 | 0 | 20 | 0 | 1 | — | — | $C_{22}$ alkyl | 400 | 420 | 500 | 500 | opaque |
| A.A. | 16 | 0 | 50 | 0 | 1 | — | — | nonylphenyl | 500 | 520 | 700 | 590 | cloudy |
| A.A. | 17 | 0 | 35 | 0 | 1 | — | — | $C_{22}$ alkyl | 600 | 590 | 1000 | 800 | cloudy |
| INV. | 18 | 0 | 25 | 0 | 1 | — | — | $C_{32}$ alkyl | 800 | 760 | 1100 | 980 | clear |
| INV. | 19 | 0 | 25 | 0 | 1 | — | — | $C_{34}$ alkyl | 800 | 740 | 1100 | 960 | clear |
| INV. | 20 | 0 | 15 | 0 | 1 | — | — | $C_{34}$ alkyl | 600 | 540 | 1300 | 1060 | clear |

$\eta$ = Brookfield viscosity
A.A. = Known Copolymer
INV. = Invention

This shampoo base is regarded as good if the Brookfield viscosity at 10 rpm and 20° C. is >1000 mPa-sec after 48 hr and the formulation is clear and transparent.

It is seen from Table II that only Tests Nos. 18–20 which employ materials of the invention, are indicated as providing good shampoo bases.

EXAMPLE 3

This Example relates to the thickening and formulation of a textile printing pie.

Toward this end, there were introduced into a glass vessel, under agitation, 441 g water, 17.5 g of a 30% active material content thickener to be tested, and 4 g antifoamant.

The agitation was carried out with the aid of a Rayneri type agitator, and was maintained constant for ¼ hr, during which period the pH was adjusted to 8 with the aid of a 30% ammonia solution.

Then 50 g of a styrene-butadiene latex, thermo-crosslinkable with the aid of melamine formaldehyde, was added, and this was mixed thoroughly for 10 min, after which 15 g of a marine blue colorant, "Sofat Neoprint", was mixed in. Thereafter, 15 g of a nonionic surfactant of the nonylphenol type, which had 4 oxyethylene groups, was added to the mixture. Agitation was conducted for 10 min.

Then the Brookfield viscosity of the textile printing pie was measured, at 10 rpm and 20° C., by means of a type "RVT" Brookfield viscosimeter equipped with a suitable mobile.

Test No. 21

The thickener tested is a copolymer of the present invention, comprised of:
a. 36 wt.% of units of methacrylic acid;
b. 55 wt.% of units of ethyl acrylate;

c. 9 wt.% of units of a methacrylate comprised of 25 oxyethylene groups and an alkyl group R' having 32 C atoms.

Test No. 22

The thickener tested is a copolymer of the present invention, comprised of:
a. 36 wt.% of units of methacrylic acid;
b. 55 wt.% of units of ethyl acrylate;
c. 9 wt.% of units of a hemimaleate comprised of 25 oxyethylene groups and an alkyl group R' having 32 C atoms.

Test No. 23

The thickener tested is a copolymer of the present invention, comprised of:
a. 36 wt.% of units of methacrylic acid;
b. 55 wt.% of units of ethyl acrylate;
c. 9 wt.% of units of a hemimaleate comprised of 25 oxyethylene groups and an alkyl group R' having 32 C atoms.

Test No. 24

The thickener tested is a copolymer of the present invention, comprised of:
a. 43 wt.% of units of methacrylic acid;
b. 51 wt.% of units of ethyl acrylate;
c. 3 wt.% of units of a methacrylate comprised of 25 oxyethylene groups and an alkyl group R' having 32 C atoms; and
d. 3 wt.% of a 50:50 (by weight) mixture of methylenebisacrylamide and ethylene glycol dimethacrylate.

The results obtained are summarized in Table III, infra.

The zeolite particles are of sizes 1–10 micron, and the suspension has an alkaline pH ($>12$).

Method

The suspension is divided into test samples of 240 g. Each sample is preserved in a 230 ml glass bottle having a hermetically sealing metal cover.

Each bottle is used in only one stabilization test. For each test, the contents of the bottle are converted to a suspension which is fluid (flowable) and homogeneous, with the aid of a system of agitation of the Rayneri type, prior to adding 1 g of the stabilizer to be tested (corresponding to 0.13 wt.% of the agent, as dry agent, based on the total weight of the suspension). Agitation is maintained for 15 min, so as to obtain an intimate mixture of the suspension to be stabilized and the stabilizer being tested.

After this time, the rheology of the system is determined with the aid of a type RVT Brookfield viscosimeter, equipped with a suitable module. The apparent viscosity $T_o$ is measured at 20° C. Readings are taken at 10 rpm and 100 rpm, following 2 min of rotation in each case. The hermetic covers are affixed to the containers of suspension thus stabilized, and the containers are allowed to "age" statically at ambient temperature for 4 days.

After this interval, the stability and rheology of the suspension are determined.

a. Stability

Stability is determined by measuring the height of the sediment at the bottom of the glass bottle, with the aid of a graduated probe. The aqueous suspension of zeolite is regarded as stable if the height of the sediment is $\leq 1$ mm.

b. Rheology

TABLE III

| TEST | | | MONOMER OF FORMULA I | | | | | $\eta$ mPa·s | COLOR | PIGMENT |
| --- | --- | --- | --- | --- | --- | --- | --- | --- | --- | --- |
| NO. | m | n | p | q | $R_1$ $R_2$ | R | R' | 10 rpm | YIELD | DISTRIBUTION |
| INV. 21 | 0 | 25 | 0 | 1 | — — | methacrylate | $C_{32}$ alkyl | 30,000 | Good | Good |
| INV. 22 | 0 | 25 | 0 | 1 | — — | hemimaleate | $C_{32}$ alkyl | 25,000 | Good | Good |
| INV. 23 | 0 | 25 | 0 | 1 | — — | hemimaleate | $C_{32}$ alkyl | 40,000 | Good | Good |
| INV. 24 | 0 | 25 | 0 | 1 | — — | methacrylate | $C_{32}$ alkyl | 45,000 | Good | Good |

$\eta$ = Brookfield viscosity
INV. = INVENTION

A textile printing pie is usable if its Brookfield viscosity measured at 10 rpm and 20° C. is $\leq 25,000$ mPa-sec, and if after application to a textile substrate and drying in a drying cabinet for several minutes at 100° C., the product displays an acceptable color yield and pigment distribution.

It is clear from Table III that the copolymers according to the invention, in Tests Nos. 21–24, result in good formulations for textile printing pies.

EXAMPLE 4

This example relates to the use of copolymers according to the invention as stabilizers for aqueous zeolite suspensions.

Toward this end, the same aqueous zeolite suspension of type 4A, containing 52.5% of zeolite (dry zeolites basis), is used for all of the tests.

The suspension has a very fluid consistency when kept agitated. In the absence of a stabilizing agent it forms a sediment in several hours, and separates into two phases, i.e., a liquid supernatant and a second phase leading to a very hard sediment which is impossible to resuspend without powerful mechanical means.

The rheology of the system is then determined by measuring the apparent viscosity of the suspension at 20° C. with the aid of a type RVT Brookfield viscosimeter equipped with a suitable module. The measurements are made at 10 and 100 rpm, following 2 min of rotation, and are annotated "T4".

The aqueous suspension is regarded as "pumpable" if the apparent viscosity measured at 10 rpm is $\leq 2500$ mPa-sec (cp).

This measurement of rheology (Brookfield viscosity) performed after 4 days of storage is repeated after a second cycle of static aging, comprising 40 days at ambient 20 temperature; these latter measurements are annotated "T40".

Test No. 25

Control test: suspension without a stabilizing agent.
The following tests employ stabilizers as follows:

Test No. 26

A copolymer of the present invention, comprised of:
a. 36 wt.% of units of methacrylic acid;
b. 58 wt.% of units of ethyl acrylate; and c. 6 wt.% of units of a hemimaleate comprised of 25 oxyethylene groups and an alkyl group R, having 32 C atoms.

Test No. 27

A copolymer of the present invention, comprised of:
a. 36 wt.% of units of methacrylic acid;
b. 55 wt.% of units of ethyl acrylate; and
c. 9 wt.% of units of a hemimaleate comprised of 20 oxyethylene groups and an alkyl group R, having 36 C atoms.

The results of the measurements of apparent Brookfield viscosity ($T_0$, T4, and T40) and of the height of the sediment, in the various tests, are summarized in Table IV, infra.

hydroxide. The apparent viscosity of each suspension is then measured on a Fann viscosimeter.

The API standard defines the apparent viscosity (Va) of a drilling fluid as that corresponding to a shear rate 1020 $sec^{-1}$, or 600 rpm rotor speed of the Fann viscosimeter.

When expressed in cp (or mPa-sec), the apparent viscosity is given by the expression:

$$Va = 0.5 \times (\text{Fann reading at 600 rpm}).$$

Test No. 28

This test is a control test, wherein the apparent viscosity of the mud is measured following 24 hr standing,

TABLE IV

| TEST | MONOMER OF FORMULA I | | | | | | | | DAYS | | | |
|------|---|---|---|---|---|---|---|---|---|---|---|---|
| | | | | | | | | | T0 | T4 | | T40 |
| NO. | m | n | p | q | $R_1$ | $R_2$ | R | R' | η mPa·s | η mPa·s | D | η mPa·s |
| T. 25 | — | — | — | — | — | — | — | — | 80–75 | Infinite | 36 mm | Infinite |
| INV. 26 | 0 | 25 | 0 | 1 | — | — | hemimaleate | $C_{32}$ alkyl | 260–150 | 1300–350 | <1 mm | 1100–290 |
| INV. 27 | 0 | 20 | 0 | 1 | — | — | hemimaleate | $C_{36}$ alkyl | 300–130 | 1300–360 | <1 mm | 1000–250 |

η mPa·s = Brookfield viscosity (mPa·sec) measured at 10 rpm and at 100 rpm
D. = Height of Sediment (mm)
T. = CONTROL
INV. = INVENTION It is clear from Table IV that the suspensions of Tests 26 and 27, which suspensions are within the scope of the invention, have, after 4 and 40 days at ambient temperature, a Brookfield viscosity (T4, T40, respectively) ≦2500 mPa-sec at 10 rpm and 20° C., and a sediment height ≦1 mm. Thus, the copolymers according to the invention are good stabilizing agents for aqueous suspensions of zeolites.

EXAMPLE 5

This Example illustrates the use of copolymers according to the invention in additives in drilling muds employing sea water, in particular additives for modifying the rheology of the muds.

For each test, three solutions are prepared, each containing 35 g clay of moderate swelling index, selected by the OCMA (Oil Company Materials Association), and 1 g $NaHCO_3$, in 350 cc of sea water.

For each of the three solutions, the solution is agitated 20 min, and then (for the tests other than the control) 5, 10, and 15 g/L, respectively, of the copolymer (dry) to be tested, are added to the three solutions, and the pH is adjusted to 9 with the aid of 35% sodium hydroxide.

After being allowed to stand 24 hr in the closed vessels, each suspension is agitated 5 min, and the pH is adjusted to 9 again, if necessary, using 35% sodium without addition of any of the copolymers.

Test No. 29

The copolymer tested is a copolymer of the present invention, comprised of:
a. 36 wt.% of units of methacrylic acid;
b. 55 wt.% of units of ethyl acrylate; and
c. 9 wt.% of units of a hemimaleate comprised of 25 oxyethylene groups and an alkyl group R, having 32 C atoms.

Test No. 30

The copolymer was a copolymer of the present invention, comprised of:
a. 36 wt.% of units of methacrylic acid;
b. 55 wt.% of units of ethyl acrylate; and
c. 9 wt.% of units of a hemimaleate comprised of 25 oxyethylene groups and an alkyl group R, having 34 C atoms.

The results of the measurements of apparent Fann viscosity from the different tests are summarized in Table V, infra.

TABLE V

| TEST | MONOMER OF FORMULA I | | | | | | | | Dose | Reading at | VISCOSITY APPARENT |
|------|---|---|---|---|---|---|---|---|---|---|---|
| NO. | m | n | p | q | $R_1$ | $R_2$ | R | R' | (*) | 600 rpm | mPa·s |
| T. 28 | — | — | — | — | — | — | — | — | 0 | 10 | 5 |
| INV. 29 | 0 | 25 | 0 | 1 | — | — | Hemimaleate | $C_{32}$ alkyl | 5 | 85 | 42.5 |
| | | | | | | | | | 10 | 162 | 81 |
| | | | | | | | | | 15 | 220 | 110 |
| INV. 30 | 0 | 25 | 0 | 1 | — | — | Hemimaleate | $C_{34}$ alkyl | 5 | 106 | 53 |
| | | | | | | | | | 10 | 200 | 100 |
| | | | | | | | | | 15 | 274 | 137 |

(*) Grams (dry) of additive per liter of drilling mud employing sea water.
T. = CONTROL
INV. = INVENTION Clay suspensions are usable in drilling muds employing sea water if their apparent Fann viscosity is >25 mPa-sec (cp). It may be seen from Table V that the drilling muds employing sea water, of Tests 29 and 30, have apparent viscosities >25 mPa-sec. Thus the copolymers of the present invention modify the initial structure of the suspension of clay in sea water, and provide this clay-filler suspension of moderate swelling index with rheological properties usable in drilling muds employing sea water.

EXAMPLE 6

This example relates to thickening of a paste-type ("cream-type") cleanser base containing a mixture of
- nonionic surfactant(s) and
- calcium carbonate of mean diameter (30 micron), of tradename "Durcal 40" (supplied by the firm Omya).

Method

Into a 1000 ml vessel equipped with a system of agitation of the Rayneri type, the following are introduced successively, under agitation:
- 330 g untreated water;
- 2.25 g of an acrylic dispersant having the tradename "Coatex P90" (supplied by the firm Coatex); and
- 375 g "Durcal 40" calcium carbonate.

The aqueous suspension of calcium carbonate thus obtained is brought to a more alkaline pH of 9.5 with 28% ammonia solution.

Then, with continuous agitation, the following are mixed in:
- 10 g of the copolymer to be tested, containing active material in the amount of 30%, and
- 3 g of a nonionic surfactant of the nonylphenol type, condensed with 10 molecules of ethylene oxide.

After 5 min of agitation, the agitation is stopped, and the immediate sedimentation ($T_0$) is estimated, with the aid of a spatula introduced into the paste-type cleanser base. The sedimentation can thereby be distinguished particularly rapidly by that fact that the spatula encounters resistance to penetration at the bottom of the vessel.

The paste-type cleanser bases are then allowed to stand for 48 hr.

At the end of the 48 hr period, the apparent Brookfield viscosity is measured at 20° C. and 10 and 100 rpm, by means of a type "RVT" Brookfield viscosimeter equipped with a suitable module, and the sedimentation (T48) of the mixture is estimated in the same manner as the immediate sedimentation.

The various copolymers tested are as follows:

Test No. 31

A copolymer known to the art, comprised of:
a. 36 wt.% of units of methacrylic acid;
b. 55 wt.% of units of ethyl acrylate;
c. 9 wt.% of units of a hemimaleate comprised of 25 oxyethylene groups and a linear alkyl group R, having 16-18 C atoms.

Test No. 32

A copolymer known to the art, comprised of:
a. 36 wt.% of units of methacrylic acid;
b. 55 wt.% of units of ethyl acrylate;
c. 9 wt.% of units of a methacrylate comprised of 25 oxyethylene groups and a linear alkyl group R, having 16-18 C atoms.

Test No. 33

A copolymer known to the art, comprised of:
a. 36 wt.% of units of methacrylic acid;
b. 55 wt.% of units of ethyl acrylate;
c. 9 wt.% of units of a hemimaleate comprised of 25 oxyethylene groups and an alkyl group R, having 22 C atoms.

Test No. 34

A copolymer known to the art, comprised of:
a. 36 wt.% of units of methacrylic acid;
b. 55 wt.% of units of ethyl acrylate;
c. 9 wt.% of units of a methacrylate comprised of 25 oxyethylene groups and an alkyl group R, having 22 C atoms.

Test No. 35

A copolymer of the present invention, comprised of:
a. 36 wt.% of units of methacrylic acid;
b. 55 wt.% of units of ethyl acrylate;
c. 9 wt.% of units of a methacrylate comprised of 25 oxyethylene groups and an alkyl group R' having 32 C atoms.

Test No. 36

A copolymer of the present invention, comprised of:
a. 36 wt.% of units of methacrylic acid;
b. 55 wt.% of units of ethyl acrylate;
c. 9 wt.% of units of a methacrylate comprised of 15 oxyethylene groups and an alkyl group R, having 36 C atoms.

The results of apparent Brookfield viscosity measurements at 10 and 100 rpm at 20° C. after 48 hr of standing, and the results of measurements of sedimentation at time zero and after standing 48 hr(T48), for the different tests, are summarized in Table VI, infra.

TABLE VI

| | TEST NO. | MONOMER OF FORMULA I | | | | | | | SEDIMEN-TATION T0 | $\eta$ BROOKFIELD VISCOSITY AFTER 48 HOURS | | SEDIMEN-TATION T48 |
|---|---|---|---|---|---|---|---|---|---|---|---|---|
| | | m | n | p | q | $R_1$ | $R_2$ | R | R' | | 10 RPM | 100 RPM | |
| A.A. | 31 | 0 | 25 | 0 | 1 | — | — | HEMIMALEATE | CETYL-STEARYL | YES | <300 | — | YES |
| A.A. | 32 | 0 | 25 | 0 | 1 | — | — | METHACRYLATE | CETYL-STEARYL | YES | <300 | — | YES |
| A.A. | 33 | 0 | 25 | 0 | 1 | — | — | HEMIMALEATE | $C_{22}$ ALKYL | YES | <300 | — | YES |
| A.A. | 34 | 0 | 25 | 0 | 1 | — | — | METHACRYLATE | $C_{22}$ ALKYL | YES | <300 | — | YES |
| INV. | 35 | 0 | 25 | 0 | 1 | — | — | METHACRYLATE | $C_{32}$ ALKYL | NO | 13000 | 6000 | NO |
| INV. | 36 | 0 | 25 | 0 | 1 | — | — | METHACRYLATE | $C_{36}$ ALKYL | NO | 20000 | 10000 | NO |

$\eta$ = BROOKFIELD VISCOSITY
A.A. = KNOWN COPOLYMER
INV. = INVENTION

A base of a paste-type cleanser is regarded as good if, after storage for 48 hr, the system thickened in the presence of nonionic surfactant(s), has an apparent Brookfield viscosity >3000 mPa-sec at 10 rpm, and has no sediment after the end of at least 48 hr. It is clear from Table VI that only Tests 35 and 36 of the invention provide formulations with high apparent viscosity and no sedimentation.

EXAMPLE 7

This Example relates to use of the copolymer of the invention as an antisedimentation agent for aqueous suspensions of coarse calcium carbonate.

Method

Into a 1000 ml beaker equipped with a system of agitation of the Rayneri type, the following are introduced, under agitation, in the order stated:
- water;
- the acrylic dispersant of molecular weight 7000 offered commercially by Coatex under the tradename "Coatex P90", which dispersant comprises active material in the amount of 40%;
- the copolymer to be tested; and finally
- a mixture of coarse calcium carbonate coming from the Salser (france) deposit comprised of 30 parts of a calcium carbonate, 29% of which comprises particles of <2 micron (commercial product of the firm Omya, under the tradename "Durcal 5"), and comprised of 70 parts of another calcium carbonate 25% comprised of particles <12 micron (commercial product of the firm omya, under the tradename "Calibrite SL").

The aqueous suspension thus produced is then maintained under strong agitation for 30 min. The agitation is stopped, and the apparent Brookfield viscosity $T_o$ of the suspension is measured at 20° C. and 10 rpm and 400 rpm, with the aid of a type "RVT" Brookfield viscosimeter equipped with a suitable module.

Following the measurement, the suspension is transferred into a 500 ml plastic jar, and is allowed to stand 8 days at 25° C. Thereafter, the consistency of the suspension is determined by introducing a spatula into the bottom of the jar. Samples having very substantial sedimentation are considered very poor, and are rated "zero". Samples having substantial sedimentation are considered poor, and are rated "1". Similarly, samples having a very adherent sediment are considered mediocre, and are rated "2", while those having an adherent but not "very adherent" sediment are considered average, and are rated "3"; those deemed "good" because they have no sediment and because they seem to have a very thick gel consistency are rated "4", and those deemed "very good", with no sediment and a gel consistency which is thick but not "very thick", are rated "5".

These characteristics of the suspension are also monitored in the same manner after 15 and 30 days storage at 25° C. At the end of 30 days storage, and after monitoring the consistency of the suspension, the suspension is subjected to mechanical agitation for 2 min, following which the apparent Brookfield viscosity ("T30") is measured at 20° C. and 10 and 100 rpm, by means of a type "RVT" Brookfield viscosimeter equipped with a suitable module.

For all tests, two beakers are employed, into which the same quantities of water, dispersant, and calcium carbonate are added, in such a way as to obtain a 75 wt.% suspension of calcium carbonate (dry material basis) in water, containing 0.035 wt.% dispersant (dry dispersant basis, with respect to the dry weight of the calcium carbonate).

In all tests, the copolymer to be tested is added at two different doses: 0.05 wt.% (dry copolymer basis, with respect to the dry weight of the calcium carbonate), in a first beaker; and 0.1 wt.% (dry copolymer basis, with respect to the dry weight of the calcium carbonate), in a second beaker.

Test No. 37

Control, with no antisedimentation agent.

In the other tests, different antisedimentation agents are used, as follows:

Test No. 38

A copolymer known to the art, comprised of:
a. 40.4 wt.% of units of methacrylic acid;
b. 59 wt.% of units of ethyl acrylate;
c. 0.6 wt.% of a crosslinking agent.

Test No. 39

A copolymer known to the art, comprised of:
a. 99.2 wt.% of units of acrylic acid;
b. 0.8 wt.% of a crosslinking agent.

Test No. 40

A copolymer known to the art, comprised of:
a. 36 wt.% of units of methacrylic acid;
b. 55 wt.% of units of ethyl acrylate;
c. 9 wt.% of units of a methacrylate comprised of 25 oxyethylene groups and a linear alkyl group R, having 16-18 C atoms.

Test No. 41

A copolymer of the present invention, comprised of:
a. 36 wt.% of units of methacrylic acid;
b. 55 wt.% of units of ethyl acrylate;
c. 9 wt.% of units of a hemimaleate comprised of 25 oxyethylene groups and an alkyl group R, having 32 C atoms.

Test No. 42

A copolymer of the present invention, comprised of:
a. 36 wt.% of units of methacrylic acid;
b. 55 wt.% of units of ethyl acrylate;
c. 9 wt.% of units of a methacrylate comprised of 25 oxyethylene groups and an alkyl group R, having 32 C atoms.

Test No. 43

A copolymer of the present invention, comprised of:
a. 36 wt.% of units of methacrylic acid;
b. 55 wt.% of units of ethyl acrylate;
c. 9 wt.% of units of a hemimaleate comprised of 25 oxyethylene groups and an alkyl group R, having 36 C atoms.

The results of the measurements of the Brookfield viscosities at 10 and 100 rpm (T0 and T30, and temperature 20° C.), and the consistencies of the suspensions after storage for 8, 15, and 30 days, respectively, at 25° C., are summarized, for all tests, in Table VII, infra.

TABLE VII

| Test | | | MONOMER OF FORMULA I | | | | | | Dose | η mPa-sec | SEDIMENTATION PROPERTIES OF THE GEL AFTER | | | η mPa-sec |
|---|---|---|---|---|---|---|---|---|---|---|---|---|---|---|
| | No. | m | n | p | q | $R_1$ | $R_2$ | R | R' | (*) | Initial | 8 Days | 15 Days | 30 Days | at 30 Days |
| T. | 37 | — | — | — | — | — | — | — | — | 0 | 3000–1500 | 0 | 0 | 0 | Infinity |
| A.A. | 38 | — | — | — | — | — | — | — | — | 0.05 | 5300–3400 | 3 | 1 | 0 | Infinity |
| | | | | | | | | | | 0.10 | 4800–2800 | 3 | 2 | 0 | Infinity |
| A.A. | 39 | — | — | — | — | — | — | — | — | 0.05 | 7200–3600 | 4 | 3 | 2 | 6800–3200 |
| | | | | | | | | | | 0.10 | 6200–2600 | 4 | 3 | 2 | 6300–2700 |
| A.A. | 40 | 0 | 25 | 0 | 1 | — | — | methacrylate | cetyl-stearyl | 0.05 | 600–490 | 0 | 0 | 0 | Infinity |
| | | | | | | | | | | 0.10 | 600–540 | 0 | 0 | 0 | Infinity |
| INV. | 41 | 0 | 25 | 0 | 1 | — | — | hemimaleate | $C_{32}$-alkyl | 0.05 | 700–450 | 4 | 2 | 2 | 1300–800 |
| | | | | | | | | | | 0.10 | 500–550 | 5 | 4 | 4 | 1100–800 |
| INV. | 42 | 0 | 25 | 0 | 1 | — | — | methacrylate | $C_{32}$-alkyl | 0.05 | 1400–620 | 5 | 4 | 4 | 1800–800 |
| | | | | | | | | | | 0.10 | 2000–930 | 5 | 5 | 5 | 2600–1200 |
| INV. | 43 | 0 | 25 | 0 | 1 | — | — | hemimaleate | $C_{36}$-alkyl | 0.05 | 400–390 | 4 | 3 | 3 | 1000–1000 |
| | | | | | | | | | | 0.10 | 800–800 | 5 | 4 | 4 | 1800–1800 |

(*) weight percent of the additive, dry additive basis, based on the dry weight of the suspension
η = Brookfield viscosity measured at 10 rpm and 100 rpm
T. = CONTROL
A.A. = A KNOWN COPOLYMER
INV. = INVENTION It is clear from Table VII that only Tests 41–43 according to the invention have sedimentation characteristics which are good ("4") or very good ("5") for a dose of 0.1 wt.% (dry basis) of the antisedimentation agent, and show Brookfield viscosities which are not excessively high.

EXAMPLE 8

This Example relates to thickening of paint-type formulations under low rates of shear.

Method

In a 1000 ml beaker equipped with an agitation device of the Reyneri type, the following are mixed, under agitation:
206 g water;
3.04 g of an acrylic dispersant of molecular weight 7000, comprised of 40% active material, which dispersant is a commercial product having tradename "Coatex P90", supplied by the firm Coatex;
1.96 g of a biocide, a commercial product having the tradename "Mergal K6N", supplied by the firm Omya; and
0.98 g of an antifoamant, a commercial product having the tradename "BYK 34", supplied by the firm BYK Chemie.

Then the following are added gradually to the mixture, under agitation:
40.27 g titanium dioxide, as a commercial product of tradename "RL 68", supplied by the firm Thann et Mulhouse;
322.10 g calcium carbonate having a mean particle diameter 3 micron, a commercial product having the tradename "Durcal 2", supplied by the firm Omya; and
211.40/g calcium carbonate having a mean particle diameter 1.5 micron, a commercial product having the tradename "Hydrocarb", supplied by the firm Omya.

The materials are dispersed for 20 min with the aid of a notched turbine mixer of diameter 70 mm and speed 1500 rpm. Then the following are introduced, under agitation:
10.02 g monoethylene glycol;
80.55 g water;
80.55 g of a styrene-acrylic binder, a commercial product having the tradename "Rhodopas DS 910", supplied by the firm Rhone-Poulenc; and
10.02 g white spirits.

The Brookfield viscosity of this unthickened paint base is measured at 0.5 rpm and 1 rpm at 20° C. on a type "RVT" Brookfield viscosimeter equipped with "module 1". Then the copolymeric thickener to be tested is added, in the amount of 2.06 wt.%, following which the pH is adjusted to 8.6 with 28% ammonia solution.

For each test, the viscosity of the paint was measured at 0.5 rpm and 1 rpm at 20° C. on a type "RVT" Brookfield viscosimeter equipped with "module 6".

Test No. 44

Control test—no thickener used.

Test No. 45

A copolymer known to the art, comprised of:
a. 40.4 wt.% of units of methacrylic acid;
b. 59 wt.% of units of ethyl acrylate;
c. 0.6 wt.% of a crosslinking agent.

Test No. 46

A copolymer of the present invention, comprised of:
a. 36 wt.% of units of methacrylic acid;
b. 55 wt.% of units of ethyl acrylate;
c. 9 wt.% of units of a methacrylate comprised of 25 oxyethylene groups and an alkyl group R, having 32 C atoms.

The results of the measurements of the Brookfield viscosities (Pa-sec) at 0.5 and 1 rpm are summarized in Table VIII, infra.

TABLE VIII

| TEST | | MONOMER OF FORMULA I | | | | | | | | η Pa·s | |
|---|---|---|---|---|---|---|---|---|---|---|---|
| | NO. | m | n | p | q | $R_1$ | $R_2$ | R | R' | 0.5 RPM | 1 RPM |
| T. | 44 | — | — | — | — | — | — | — | — | 0.08 | 0.08 |
| A.A. | 45 | — | — | — | — | — | — | — | — | 500 | 300 |

TABLE VIII-continued

| TEST | MONOMER OF FORMULA I | | | | | | | | $\eta$ Pa·s | |
|---|---|---|---|---|---|---|---|---|---|---|
| NO. | m | n | p | q | R₁ | R₂ | R | R' | 0.5 RPM | 1 RPM |
| INV. 46 | 0 | 25 | 0 | 1 | — | — | Methacrylate | $C_{32}$ alkyl | 700 | 500 |

$\eta$ = BROOKFIELD VISCOSITY
T = CONTROL
A.A. = ART KNOWN
INV. = INVENTION

It is clear from Table VIII that the paint formulation of Test No. 46 of the invention provides a much higher viscosity at low speed gradient and low shear gradient than the formulation of Test No. 45 according to the known art.

Further, the rheological properties conferred by the copolymeric thickener according to the invention are very close to those of top quality paints, viz. a very pasty consistency at rest but flowability under very weak agitation.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A copolymer which is water-soluble or moderately water-soluble and which may be crosslinked, comprising:
   (a) units of at least one monomer having ethylenic unsaturation and having at least one carboxylic acid group, which monomer is selected from the group consisting of monoacids, diacids, the anhydrides of carboxylic acids, and the hemiesters of diacids;
   (b) optionally, unit(s) of at least one monomer having ethylenic unsaturation and not having a carboxylic acid group selected from the group consisting of the esters, amides, and nitriles of (meth)acrylic acid, or selected from the group consisting of vinyl acetate, styrene, methylstyrene, diisobutylene, vinylpyrrolidone, and vinylcaprolactam;
   (c) units of at least one monomer having an oxyalkylated moiety, which monomer has ethylenic unsaturation and is terminated by a hydrophobic fatty chain, said monomer having formula I:

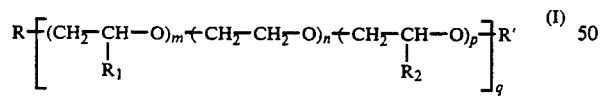

where m and p represent numbers of oxyalkylene groups each $\leq 100$;
   n represents the number of oxyethylene groups $\leq 100$;
   q represents a number at least equal to 1 such that $q(n+m+p) \leq 100$;
   R₁ represents hydrogen or a methyl group;
   R₂ represents hydrogen or a methyl group;
   R' represents hydrophobic fatty hydrocarbon chain of at least 26 carbon atoms; and
   R represents an unsaturated polymerizable group selected from the group consisting of vinyl group containing moieties, methacryloyl, maleoyl, itaconoyl, crotonyl, an unsaturated urethane moiety, hemiester maleoyl, hemiester itaconoyl, $CH_2=CHCH_2-O-$, methacrylamido and substituted methacrylamido; and
   (d) optionally, unit(s) of at least one monomer having at least two sites of ethylenic unsaturation selected from the group consisting of ethylene glycol dimethacrylate, 2,2-dihydroxymethylbutanol triacrylate, allyl acrylate, methylenebis(meth)acrylamide, tetraallyloxyethane, triallyl cyanurate, and allyl ethers obtained from polyols.

2. The copolymer of claim 1, wherein said monomer (a) is acrylic acid, methacrylic acid, crotonic acid, isocrotonic acid, cinnamic acid, itaconic acid, fumaric acid, maleic acid, citraconic acid, maleic anhydride or a $C_{1-4}$ monoester of maleic or itaconic acid.

3. The copolymer of claim 1, wherein said monomer (b) is methyl, ethyl, butyl or 2-ethylhexyl(meth)acrylate.

4. The copolymer of claim 1, wherein said monomer (d) is an allyl ether of pentaerythritol, sorbitol or sucrose.

5. The copolymer of claim 1, wherein said unsaturated polymerizable group R, as an unsaturated urethane, is (meth)acrylurethane, α,α-dimethyl-m-isopropenylbenzylurethane or allylurethane.

6. The copolymer according to claim 1, wherein in monomer (c) the number of C atoms in group R' is at least 30.

7. The copolymer according to claim 1, wherein in monomer (c) of formula I:

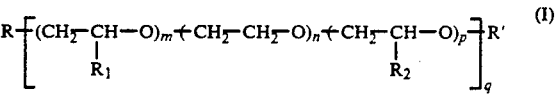

m, p, and n are each in the range 10–70;
q is a number at least equal to 1, such that $10 \leq q(n+m+p) \leq 70$; and the number of C atoms in the group R' is 28.

8. The copolymer according to claim 1, which is comprised of the following:
   15–98 wt.% of monomer unit (a); 0–83 wt.% of monomer unit (b) selected from the group consisting of an ester of (meth)acrylic acid selected from the group consisting of methyl, ethyl, butyl and 2-ethylhexyl(meth)acrylate, acrylonitrile, vinyl acetate, styrene, methylstyrene, diisobutylene, vinylpyrrolidone, and vinylcaprolactam; 2–18 wt.% of monomer unit (c); and 0–5% of monomer unit (d).

9. The copolymer according to claim 8, wherein the proportions of the constituent units are as follows:
   (a) 20–50 wt.%;
   (b) 47–77 wt.%;
   (c) 3–10 wt.%;
   (d) 0–3%.

10. The copolymer according to claim 1, wherein monomer (a) is selected from the group consisting of acrylic acid, methacrylic acid, and itaconic acid.

11. The copolymer according to claim 1, wherein monomer (b) is selected from the group consisting of (meth)acrylic esters having alkyl groups of 1–4 C atoms.

12. The copolymer according to claim 1, wherein the vinyl group of moiety R is acryloyl, a vinylphthaloyl, a hemiester phthaloyl, acrylamido or substituted acrylamido and wherein said unsaturated urethane is (meth)acrylurethane, $\alpha,\alpha$-dimethyl-m-isopropenyl-benzylurethane or allylurethane.

* * * * *

UNITED STATES PATENT AND TRADEMARK OFFICE
CERTIFICATE OF CORRECTION

PATENT NO. : 5,294,693

DATED : March 15, 1994

INVENTOR(S) : Egraz et al.

It is certified that error appears in the above-identified patent and that said Letters Patent is hereby corrected as shown below:

COLUMN 2, line 1 "$A_a-B_bC_c-D_d,$" should read --$A_a - B_b - C_c - D_d,$--.

COLUMN 6, line 14, "rates($^{-1}$) are" should read --rates ($s^{-1}$) are--.

COLUMN 9, lines 18-19, "b.  55 wt.% of units
           c.   9 wt.% of units" should read --b.  48 wt.% of units
   c.  16 wt.% of units--.

COLUMN 9, line 47, "20°C is $\leq$ 25,000" should read --20°C is $\geq$ 25,000--.

Signed and Sealed this

Ninth Day of May, 1995

Attest:

*Attesting Officer*

BRUCE LEHMAN

*Commissioner of Patents and Trademarks*